United States Patent [19]

Marchant

[11] Patent Number: 5,112,457
[45] Date of Patent: May 12, 1992

[54] PROCESS FOR PRODUCING HYDROXYLATED PLASMA-POLYMERIZED FILMS AND THE USE OF THE FILMS FOR ENHANCING THE COMPATIBLITY OF BIOMEDICAL IMPLANTS

[75] Inventor: Roger E. Marchant, Shaker Hts., Ohio

[73] Assignee: Case Western Reserve University, Cleveland, Ohio

[21] Appl. No.: 556,740

[22] Filed: Jul. 23, 1990

[51] Int. Cl.$^5$ .............................................. H05F 3/00
[52] U.S. Cl. ................................. 204/165; 525/329.6; 525/337; 525/366; 525/367
[58] Field of Search ..................... 525/329.6, 337, 366, 525/367; 204/165

[56] References Cited

U.S. PATENT DOCUMENTS

| | | | |
|---|---|---|---|
| 4,199,448 | 4/1980 | Johnson et al. | 210/654 |
| 4,560,458 | 12/1985 | Ueno et al. | 204/165 |
| 4,705,544 | 11/1987 | Okita et al. | 55/16 |
| 4,868,254 | 9/1989 | Wong | 525/539 |

*Primary Examiner*—John F. Niebling
*Assistant Examiner*—Steven P. Marqis
*Attorney, Agent, or Firm*—Fay, Sharpe, Beall, Fagan, Minnich & McKee

[57] ABSTRACT

The present invention is directed to a process for synthesizing hydroxylated plasma-polymerized films, as well as the hydroxylated plasma-polymerized films produced by the process of the invention. In addition, the present invention is directed to the use of hydroxylated plasma-polymerized films produced by the process of the invention for enhancing the compatibility and/or implantability of biomedical implants and/or devices.

14 Claims, 3 Drawing Sheets

PROCESS FOR PRODUCING HYDROXYLATED PLASMA-POLYMERIZED FILMS AND THE USE OF THE FILMS FOR ENHANCING THE COMPATIBLITY OF BIOMEDICAL IMPLANTS

BACKGROUND OF THE INVENTION

The present invention relates to a process for producing hydroxylated plasma-polymerized films, and the hydroxylated plasma-polymerized films produced by the process of the invention. In addition, the present invention is directed to the use of the hydroxylated plasma-polymerized films produced by the process of the invention for enhancing the compatibility and/or implantability of blood-contacting biomedical implants and devices.

More particularly, the present invention relates to a process for producing films of plasma-polymerized polymers, such as plasma-polymerizing N-vinyl-2-pyrrolidone (PPNVP), deposited on the surface of various implantable devices, and reducing the carbonyl groups present on the crosslinked plasma-polymerized polymer, i.e. the plasma-polymerized N-vinyl-2-pyrrolidone (a polymer which is rich in carbonyl groups), to hydroxyl groups through the use of an aqueous solution of sodium borohydride. By increasing the hydroxyl content of the plasma-polymerized N-vinyl-2-pyrrolidone polymer, the surface upon which the polymer has been deposited exhibits, either alone or in combination with other surface modification agents, increased blood compatibility (i.e. exhibits a decrease in surface induced thrombosis) thereby producing an effective interface for implanted material.

Along this line, surface activated thrombosis and associated sequelae is a major problem which is common to all blood contacting synthetic implants and biomedical devices. All currently used blood-contacting biomaterials suffer from problems associated with surface induced thrombosis such as thrombotic occlusion of the device, and the generation of thromboemboli. The mechanisms of coagulation and platelet activation are common to all "foreign" surfaces in contact with blood, although the kinetics of the reactions are affected by the site of implantation, and the surface area and properties of the material. Examples include implants such as heart valves, ventricular assist devices, vascular grafts; extracorporeal systems such as cardiopulmonary bypass, and hemodialysis; and invasive treatment and diagnostic systems which involve the use of various catheter systems. Other vascular implants such as small diameter vascular grafts are currently impracticable, because of thrombosis problems. Currently, recipients of vascular implants and devices usually undergo aggressive collateral treatment with anticoagulant, antiplatelet and/or fibrinolytic agents to minimize thrombosis. These therapies are not completely effective and the patient may also suffer from significant adverse side effects, which include bleeding and thrombocytopenia.

The lack of a suitable non-thrombogenic biomaterial (biologic or synthetic) has been responsible for limiting progress and success of existing devices and the development of new devices for long-term cardiovascular applications. In this regard, the surface of a biomaterial is the most important factor that affects blood compatibility behavior. This may be the surface of an implanted artificial device such as a heart valve or vascular graft, a blood monitoring device such as a biosensor, or an extracorporeal system such as cardiopulmonary bypass. The potential clinical success of these implantable devices would be greatly enhanced by a nonthrombogenic biomaterial.

A review of the prior art directed to the compatibility of the surface structure of the implantable device indicates that the composition and structure of solid polymer surfaces dominate such properties as (i) wetability (Zisman, W. A., In Adhesion Science and Technology, Lee, L. H., Eds., Plenum Press, N.Y., pp. 55, 1975; Anderson, A. W., Physical Chemistry of Surfaces, John Wiley, N.Y., 1982; and, Cherry B. W., Polymer Surfaces, Cambridge University Press, N.Y., 1981), (ii) adhesion (Anderson, A. W., Physical Chemistry of Surfaces, John Wiley, N.Y., 1982; Cherry B. W., Polymer Surfaces, Cambridge University Press, N.Y., 1981; and, Mittal, K. L., In Adhesion Science and Technology, Lee, L. H., Ed., Plenum Press, N.Y., p. 129, 1975), (iii) friction (Anderson, A. W., Physical Chemistry of Surfaces, John Wiley, N.Y., 1982; and Cherry B. W., Polymer Surfaces, Cambridge University Press, N.Y., 1981), (iv) permeability (Stannet, V., Hopfenberg, H. B., Williams, J. L., In Structure and Properties of Polymer Films, Lenz R. W., Stein, R. S., Eds., Plenum Press, N.Y., p. 321, 1973) and biocompatibility (Anderson, J. M., Kottke-Marchant, K., CRC Crit. Rev. Biocompat., 1, 111, 1985; and Salzman, E. W., Interaction of the Blood with Natural and Artificial Surfaces, Dekker, New York, 1981) Consequently, procedures for the surface modification of materials to improve interfacial properties are of considerable technological importance. One approach has been the use of plasma-polymerization (Boenig, H. V., Plasma Science and Technology, Cornell University Press, Ithaca, 1982) also referred to as glow discharge polymerization.

Plasma-polymerized films can be prepared with a wide range of compositions (Yasuda, H., Plasma Polymerization, Academic Press, New York, 1985) and surface energies (Yasuda, H., Plasma Polymerization, Academic Press, New York, 1985; and Haque, Y., Ratner, B. D., J. Appl. Polym. Sci., 32, 4369, 1986) through the choice of the monomer and the discharge reaction conditions. The deposition is largely independent of the substrate materials and is surface specific, so that a polymer (or other material) can be modified with little effect to its bulk properties.

However, while plasma-polymerization does have several attractive advantages over other methods of surface modification, there is a significant lack of chemical control over the polymer product. Reactions in the low-temperature plasmas are dominated by electron impact events such as ionization and dissociation, with active species reacting and recombining in the plasma and at the substrate surface. Because of the high energies involved in the process, this technique does not provide films with well-defined structures and specific functional groups (Soluble polymers often with high molecular weights can be prepared using the related technique of plasma-initiated polymerization. For a recent detailed report on this technique, see: Paul, C. W., Bell, A. T., Soong, D. S., Macromolecules, 20, 782, 1987). In addition, plasma-polymerized films prepared from monomers with oxygen or nitrogen functional groups invariably are poly-functional, cross-linked, heterogeneous polymers.

Nevertheless, the objective of the studies of the present inventors was to prepare plasma-polymerized films with a well-defined functional group that could serve as a reactive site for further modification. The common approaches for introducing specific functional groups into plasma polymers have been to vary the monomer and discharge conditions or to use or include a gas such as $CO_2$ (Inagaki, N., Matsunaga, M., *Polym. Bull.*, 13, 349, 1985) or $NH_3$ (Nakayama, Y., Takahagi, T., Soeda, F., Hatada, K., Nagaoka, S., Suzuki, J., Ishitani, A., *J. Polym. Sci., Polym. Chem.*, 26, 559, 1988), which tend to increase carboxyl and amine groups, respectively. However, these reactions do not normally proceed to high yield with respect to a specific functional group. (Nakayama, Y., Takahagi, T., Soeda, F., Hatada, K., Nagaoka, S., Suzuki, J., Ishitani, A., *J. Polym. Sci., Polym. Chem.*, 26, 559, 1988) have reported that primary amine in $NH_3$ plasma treated polystyrene was 15%–20% of total nitrogen content. Plasma treatment, as opposed to plasma-polymerization, refers to the use of a non-polymerizing gas plasma to oxidize or otherwise directly treat a polymer surface. No polymer is formed by this process, but the surface composition becomes significantly different from the bulk polymer.

A novel alternative approach to functionalize a plasma-polymerized material is to take advantage of the functional group that is easily generated in the process: carbonyl groups. Plasma polymers derived from oxygen-containing monomers are invariably rich in carbonyl, regardless of the initial monomer structure. Thus, if a polymer or nonorganic was surface modified by plasma-polymerization, carbonyl groups in the modified layer could then be derivatized to introduce a desired functional group.

The major difficulty of this approach is associated with the very poor solubility of cross-linked plasma polymers in organic solvents. Derivatization has to be accomplished across an ill-defined interface between a constrained solid polymer and the liquid reaction medium. However, Whitesides et al. (Rasmussen, J. R., Stedronsky, E. R., Whitesides, G. M., *J. Am. Chem. Soc.*, 99, 4736, 1977; Rasmussen, J. R., Bergbreiter, D. E., Whitesides, G. M., *J. Am. Chem. Soc.*, 99, 4746, 1977), carried out several derivatization procedures on chromic acid oxidized polyethylene. These included the surface reduction of carboxyl to hydroxyl by using diborane in THF and by using an etheral solution of lithium aluminum hydride (Rasmussen, J. R., Stedronsky, E. R., Whitesides, G. M., *J. Am. Chem. Soc.*, 99, 4736, 1977). More recently, Dias and McCarthy (Dias, A. J., McCarthy, T. J., *Macromolecules*, 17, 2529, 1984) reported a series of surface-specific (i.e., 300-Å depth) derivatization reactions performed on fluorocarbon and fluorochlorocarbon polymers. In each of these previous studies the objective was to introduce specific functional groups into the surface of relatively unreactive solid polymers. Their results hint that derivatization of a plasma-polymerized polymer may possibly be feasible, depending on the effect of the additional geometric constraint imposed by the cross-links in a plasma polymer.

In the present invention, the applicants have focused on the formation of hydroxyl groups by the reduction of the carbonyl groups in plasma-polymerized polymers such as N-vinyl-2-pyrrolidone (PPNVP), a polymer which is rich in carbonyl groups. To applicants' knowledge, the bulk reduction or chemical modification of a cross-linked plasma-polymerized polymer has not been previously reported and/or utilized, particularly for enhancing the surface compatibility of biomedical implants. While the invention shall be described in connection with plasma-polymerized N-vinyl-2-pyrrolidone, it is well understood by those skilled in the art that the process and techniques disclosed herein are not limited to N-vinyl-2-pyrrolidone and may also be applicable to other oxygen-containing monomers such as ethanol and acetone.

SUMMARY OF THE INVENTION

In one aspect, the present invention relates to a process for producing a hydroxylated plasma-polymerized polymer, such as hydroxylated plasma-polymerized N-vinyl-2-pyyrolidone, comprising the steps of synthesizing a plasma-polymerized polymer, such as plasma-polymerized N-vinyl-2-pyyrolidone, utilizing a plasma-polymerization process and adding to the plasma-polymerized polymer an aqueous solution of a metal hydride, such as sodium borohydride, thereby reducing the carbonyl groups present in the plasma-polymerized polymer to hydroxyl groups. The functional hydroxyl groups incorporated into the plasma-polymerized polymer then allow the polymer to be more readily accessible to further modifications including immobilization reactions. As a result, the modification of the carbonyl groups to hydroxyl groups, greatly enhances the controllability of the surface chemistry of the polymer and/or the surface of the biomedical device coated with the polymer.

In an additional aspect, the present invention is directed to the modified (i.e. hydroxylated) plasma-polymerized polymer (i.e. hydroxylated plasma-polymerized N-vinyl-2-pyyrolidone) produced by the process of the invention.

In a further aspect, the present invention relates to a process for modifying the blood contact surface of a biomedical device in order to make the surface more readily accessible to various reactions, such as immobilization reactions, which enhance the compatibility of the blood contact surface of the device. The process involves the steps of treating the blood contact surface of the biomedical device with an argon plasma glow discharge to activate (i.e. to produce the formation of surface localized free radicals) the surface, depositing on the activated surface by means of plasma assisted polymer deposition, a plasma-polymerized polymer such as a plasma-polymerized N-vinyl-2-pyrrolidone film, and adding to the plasma-polymerized polymer deposited on the blood contact surface of the biomedical device an aqueous solution of a metal halide, such as sodium borohydride. The aqueous solution of the metal halide (i.e. $NaBH_4$) reduces carbonyl groups present in the plasma-polymerized polymer to hydroxy groups, thereby providing a medium for further modification in order to enhance the compatibility of the blood contact surface.

In a still further aspect, the present invention is directed to the modified blood contact surface produced by the process of the present invention.

BRIEF DESCRIPTION OF THE DRAWINGS

The following is a brief description of the drawings which are presented for the purpose of illustrating the invention and not for the purpose of limiting same.

DETAILED DESCRIPTION OF THE INVENTION

Figure 1:
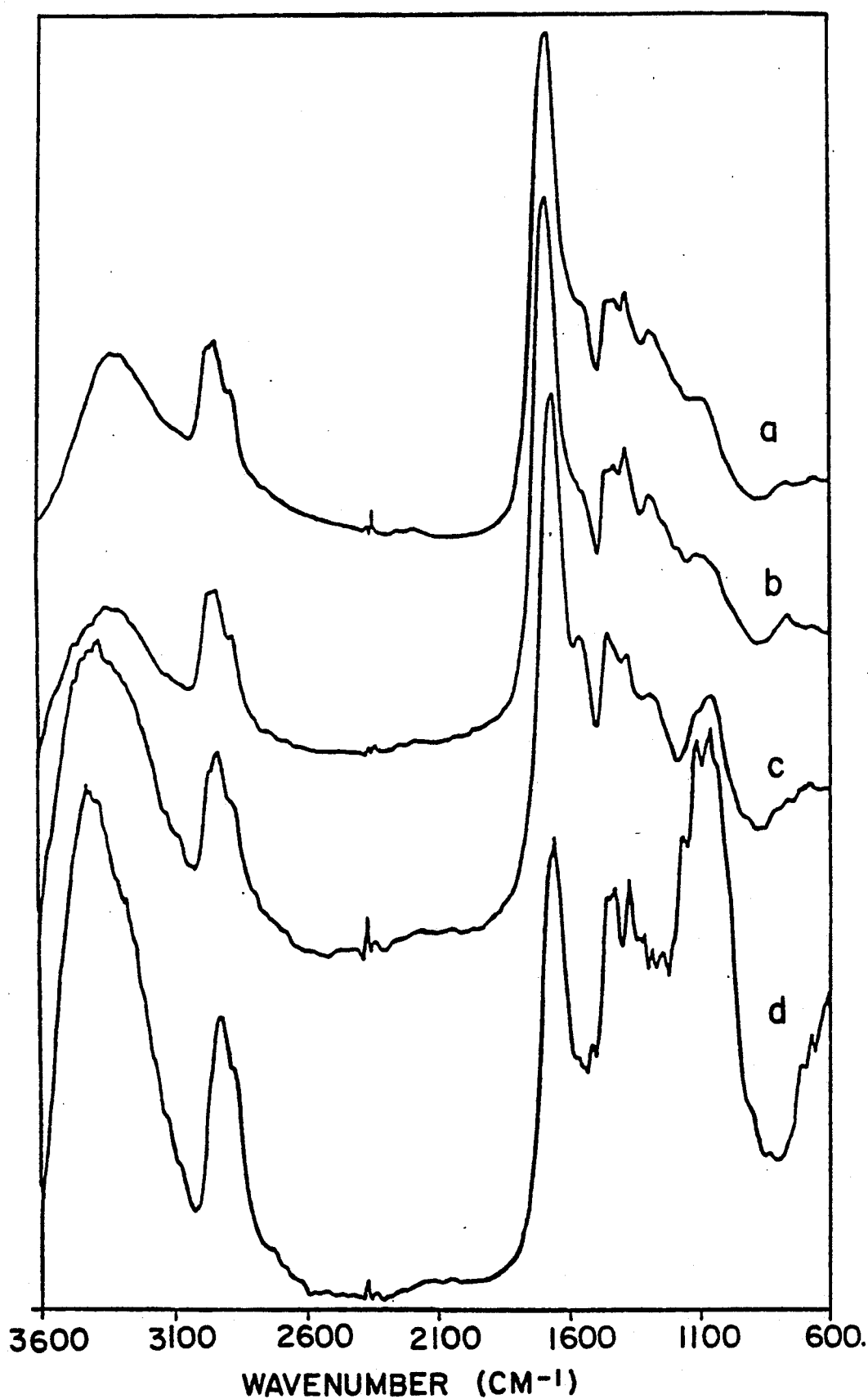
FIG. 1 is a graph showing the FT-IR spectra, 3600–600 $cm^{-1}$ region, of PPNVP and reduced PPNVP samples. (a) Spectrum of PPNVP prepared at 30 watts discharge power, 0.03 torr reaction pressure and 0.28 $cm^3$(STP)$min^{-1}$ monomer flow rate. (b) Spectrum of PPNVP reduced in film form by 1 mol LiAlH4 in THF at room temperature for 68 hours. (c) Spectrum of PPNVP reduced in film form by 0.26 mol aqueous solution of NaBH4 at room temperature for 30 hours. (d) Spectrum of PPNVP reduced in suspension form by 0.26 mol aqueous solution of NaBH4 at room temperature for 30 hours.

The present invention is directed to a process for synthesizing hydroxylated plasma-polymerized films, as well as the hydroxylated plasma-polymerized films produced by the process of the invention. In addition, the present invention is directed to the use of hydroxylated plasma-polymerized films produced by the process of the invention for enhancing the compatibility and/or implantability of biomedical implants and/or devices.

Specifically, the present invention is directed to a process for producing films of plasma-polymerized polymers, such as plasma-polymerized N-vinyl-2-pyrrolidone, deposited on the surface of a various substrates utilized in the construction of biomedical devices, and reducing the carbonyl groups present on the plasma-polymerized polymer to hydroxyl groups through the use of metal halides, such as sodium borohydride, in aqueous solution. By increasing hydroxyl content of the plasma-polymerized polymer, the surface upon which the polymer has been deposited may be more easily chemically modified in order to enhance the overall compatibility of the implanted device.

The formation of hydroxyl (-OH) groups in plasma-polymerized polymers, such as N-vinyl-2-pyrrolidone (PPNVP), by the reduction of the carbonyl (c=O) groups with metal hydrides (i.e. sodium borohydride) in an aqueous solution, is demonstrated by the following general formula:

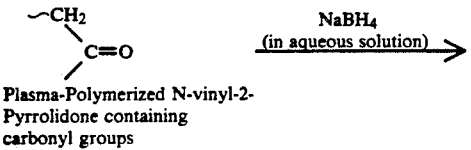

Plasma-Polymerized N-vinyl-2-Pyrrolidone containing carbonyl groups $\xrightarrow{\text{NaBH}_4 \text{ (in aqueous solution)}}$ -continued

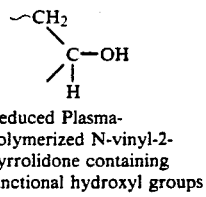

Reduced Plasma-Polymerized N-vinyl-2-Pyrrolidone containing functional hydroxyl groups As a result, the present inventors have developed a process for producing an optimal polymer (film) which not only effectively coats the surface of the implant and/or biomedical device, but also provides functional groups (i.e. hydroxyls) on the polymer (i.e. film) surface which are readily accessible for further modifications including immobilization reactions.

The functional group(s) (i.e. hydroxyls) allow for the binding of the blood compatible agents, such as fractionated, highly active heparin oligosaccharides, which are believed to inhibit surface induced thrombosis, thereby greatly extending the functional life span of the implanted biomedical device.

The overall surface modification of the present invention inhibits thrombosis formation by providing the surface of the biomedical device, which may be composed of a wide range of support materials including polyethylene, poly(ether-urethanes) (also referred to as segmented polyurethanes), and polysiloxane-type silicone elastomers, a number of common clinically used biomedical polymers, with a plasma solvated non-thrombogenic microenvironment. This is accomplished by treating the support surface with an aqueous plasma glow discharge to activate the surface, followed by the plasma assisted polymer deposition of an oxygen-containing monomer such as N-vinyl-2-pyyrolidone (NVP), ethanol and acetone. The carbonyl groups in the film are then reduced to alcohol groups by chemical reduction using an aqueous solution of sodium borohydride.

The alcohol groups present in the modified (i.e. reduced) hydrophilic PPNVP films coating the surfaces of the clinically relevant implant or device then act as functional groups for additional modification, such as for the immobilization of various agents which minimize the undesirable interaction (i.e. coagulation, platelet adhesion, non-specific protein adsorption, etc.) with blood components. By producing a plasma-polymerized PPNVP thin film and modifying the carbonyl groups present in the PPNVP film to include the alcohol (hydroxyl) functional groups, a high degree of surface control is generated. As a result, the surface modification procedure of the present invention provides the basis for producing blood contacting biomaterials which process non-thrombogenic properties.

A more detailed discussion concerning various critical steps of the process of the present invention, including the enhanced operating parameters, etc., are set forth below in the following example. While the following example is directed to the reduction of plasma-polymerized N-vinyl-2-pyrrolidone, the process of the present invention is not limited to N-vinyl-2-pyrrolidone and is applicable to other oxygen-containing monomers such as ethanol and acetone.

EXAMPLE 1

Experimental Section

MATERIALS. N-vinyl-2-pyrrolidone (NVP, from Aldrich Chemical Co., Milwaukee, Wis.) was distilled under vacuum, degassed three times by the freeze(dry ice/acetone)-thaw technique under vacuum, and stored under argon at −4° C. Poly(vinyl alcohol) (PVA, 100% hydrolyzed, MW 14000, from Aldrich Chemical Co., Milwaukee, Wis.) was finely ground, dried under vacuum at 50° C. for 12 h, and stored in a desiccator over fresh phosphorus pentoxide. 1-Hexadecanol (Aldrich Chemical Co., Milwaukee, Wis.) was recrystallized (mp, 55° C.) from hot ethanol and stored under argon in the refrigerator. Acetic anhydride (99+% grade, Aldrich Chemical Co., Milwaukee, Wis.) was distilled and stored over 3A sieves and under argon. Potassium thiocyanate (99+%, ACS grade, Aldrich Chemical Co., Milwaukee, Wis.) was finely ground and stored in the desiccator. Potassium bromide (IR grade, Fisher Science Co., Pittsburgh, Pa.) was finely ground, dried overnight at 140° C., and stored in the desiccator. Metal hydride reducing agents, sodium borohydride (99%, Aldrich Chemical Co., Milwaukee, Wis.), lithium aluminum hydride (1.0 mol., solution in THF, Aldrich Chemical Co., Milwaukee, Wis.), and other chemicals were used as received.

Cleaned glass microslides (75×25 mm$^2$) were used as substrates for the plasma-polymerization. The glass slides were cleaned by using a freshly prepared solution of H$_2$SO$_4$ and Nochromix (Godax Laboratories, Inc., NY, N.Y.), thoroughly washed with distilled water and then refluxing acetone vapor in a soxhlet extraction system for 24 hours, and dried at 80° C. under vacuum.

Plasma-Polymerization of NVP

Thin films of plasma-polymerized N-vinyl-2-pyrrolidone (PPNVP) were prepared by using an inductively coupled radio frequency (13.56 MHz) glow discharge in a flow-through Pyrex reactor system (Marchant, R. E., Yu, D., Khoo, C, *J. Polym. Sci., Polym. Chem.*, Vol. 27, pp. 881–895, 1989). NVP monomer was plasma-polymerized for 2 hours at 30 watts net discharge power, a reaction pressure of $3 \times 10^{-2}$ Torr, and a monomer flow rate of 0.28 cm$^3$ (STP) min$^{-1}$. Under these conditions, hydrophilic polymer films of PPNVP approximately 1.5 μm thick were obtained on glass slides. At the end of the reaction period, the base pressure (ca. $5 \times 10^{-1}$ Torr) was restored and maintained for one hour. The chamber pressure was then raised to atmospheric with argon. PPNVP films on glass slides were removed from the reactor and stored in a desiccator over phosphorus pentoxide.

Reduction of PPNVP

An aqueous solution (200 mL, 0.26 mol) of sodium borohydride was freshly prepared and stirred slowly at room temperature. A PPNVP film sample supported on a glass slide was immersed in the solution and left stirring for the selected reaction time (0.5–48 hours). Reactions were performed at room temperature under a constant argon purge.

After reaction, the polymer was sonicated in distilled water, washed three times in distilled water, and then left in stirring water for 12 hours. Polymer was then washed twice in acetone and vacuum dried at 80° C. for 12 hours. Dry polymer was stored in a desiccator over phosphorus pentoxide. The reduction was repeated with a suspension of PPNVP. A PPNVP film was removed from the glass slide by sonication in distilled water and then dried under vacuum at 80° C. for 12 hours. The dry polymer was finely ground and added to the reducing solution. The reaction was carried out for 30 hours. After reaction, the polymer was filtered from solution and then washed and dried as before.

Infrared Spectroscopy

Spectra of polymer samples were obtained by using the KBr pellet method with a Digilab FTS-14 Fourier transform infrared spectrometer equipped with a TGS detector. Over 100 sample scans and reference scans at a resolution of 8 cm$^{-1}$ were averaged and subtracted. IR spectra were then transferred to a DEC VAX 11/780 for data processing.

Materials used in the preparation of KBr pellets were preground, dried, mixed, and ground together before being pressed into a pellet under vacuum. In the case of PVA samples, repeated grinding and molding were required to obtain a satisfactory pellet.

Quantitative estimation of the increased hydroxyl content in reduced PPNVP samples was accomplished by using the relative (integrated) absorbance ratio method with added internal standard (potassium thiocyanate). 1-Hexadecanol and PVA were used as reference compounds for primary and secondary alcohol groups, respectively. The percent primary and secondary alcohol contents in plasma-polymerized samples was estimated by using a curve-fitting procedure based on linear combinations of the two reference compounds (Antoon, M. K., Koenig, J. H., Koenig, J. L., *Appl. Spectrosc.*, 31, 518, 1977). Using this result, the increased hydroxyl content could then be estimated from the standard calibration curves of the two model compounds, subtracting the result obtained for the original PPNVP control.

The calibration curves for the model compounds were obtained from the ratio of the integrated absorbance at 1180–980 cm$^{-1}$ (from $\nu(C-O)$ in COH) to the integrated absorbance at 2150–2000 (from KSCN), plotted against the concentration ratio of model compound to KSCN. The standard calibration curve for 1-hexadecanol was linear and passed through the origin (correlation coefficient=1.000). The calibration curve for PVA showed a slight deviation from linearity, with an intercept close to zero for the concentration range employed (correlation coefficient=0.98).

Hydroxyl contents (mmol/g) in PVA and 1-hexadecanol reference compounds were quantified by using the analytical method of Stetzler and Smullin (Stetzler, R. S., Smullin, C. F., *Anal. Chem.*, 34, 194, 1962). This method involves the acid-catalyzed esterification of alcohol groups with excess acetic anhydride, followed by the addition of aqueous pyridine solution to hydrolyze unreacted reagent. Hydroxyl content was calculated from the titration of test solutions and blank reference against standardized potassium hydroxide solution This analysis gave 21.46 mmol/g (calculated value=22.7) for PVA and 4.05 mmol/g (calculated value=4.13) for 1-hexadecanol.

RESULTS AND DISCUSSION

Reduction Reaction

Nucleophilic metal hydrides have been widely used for organic reductions in solution. However, in the applicants' preliminary experiments on PPNVP, using LiAlH$_4$ in anhydrous THF, no reaction was detected. A large excess of LiAlH$_4$ and long reaction times provided no change to the infrared spectrum of PPNVP (see FIG. 1a,b). The absence of detectable reaction in this heterogeneous system was attributed to the lack of polymer solvation.

PPNVP, like any plasma-polymerized organic material, is a cross-linked polymer with an irregular complex structure; however, PPNVP is hydrophilic and will absorb up to 51.7% water by weight (Yu, D., Marchant, R. E., unpublished result). This suggested that the reduction of carbonyl groups in the polymer should be feasible in aqueous or other polar media. Sodium borohydride is a metal hydride that can be used in polar solvents for the selective reduction of aldehydes and ketones (Rerick, M. N., *In Reduction, Techniques, and Applications in Organic Synthesis*, Augustine, R. L., Ed., Dekker, New York, 1968, Ch. 1; and, Adams, C. Gold, V., Reuben, D. M. E., *J. Chem. Soc. Perkin II*, 1466, 1977). Indeed, the reduction by NaBH$_4$, unlike LiAlH$_4$, requires the presence of an electrophilic catalyst such as a porotic solvent. The reaction with carbonyl groups is believed to occur by hydride ion transfer to the carbonyl carbon with prior protonation of the carbonyl oxygen (House, M. O., *Modern Synthetic Reactions*, second edition, Benjamin/Cummings, Menlo Park, Ch. 2, 1977). NaBH$_4$ will react directly with water but very slowly (Brown, H. C.; Ichikawa, K., *J. Am. Chem. Soc.*, 83, 4372, 1961). In contrast, the applicants' attempts to conduct the reaction in either anhydrous methanol or 2-propanol were unsuccessful, since both alcohols reacted with NaBH$_4$ at room temperature to form white precipitate within one and six hours, respectively.

The effect of using NaBH$_4$/water rather than LiAlH$_4$/THF to reduce carbonyl to hydroxyl can be seen by comparing parts (a)-(d) of FIG. 1. Prominent features of these spectra are the strong carbonyl ($v$(C=O), ca. 1670 cm$^{-1}$) and hydroxyl stretching absorptions ($v$(O—H), ca. 3500-3200 cm$^{-1}$. This latter band is complicated by contributions from $v$(N—H) absorptions derived from any amide or amine groups present in the polymer.

In the reduced PPNVP samples (FIG. 1c,d), the "hydroxyl peak" (3500-3200 cm$^{-1}$) has increased, while the intensity of the carbonyl absorption has decreased compared with that of underivatized PPNVP. However, the most obvious change was the concomitant appearance of a strong absorption at 1180-980 cm$^{-1}$ attributed to $v$(C—O) in C—OH, indicating the formation of hydroxyl groups. Other notable spectral features of the reduced polymer were in the 1500-1300 cm$^{-1}$ region, which contains overlapping bands derived from C—H deformation absorptions such as methylene C—H deformation at 1455 cm$^{-1}$ and $\delta$(C—H) in CH$_2$ adjacent to a carbonyl group at 1415 cm$^{-1}$.

FIG. 1c shows that hydroxyl groups were formed by reduction of the PPNVP film, but the figure also shows that the reaction did not go to completion, with the carbonyl absorption still the most prominent. The cause of the observed inhibition was not clear, with several possible contributing factors such as geometric constraints, product inhibition, surface area, and mixing efficiency. In these film experiments, stirring was kept relatively slow to avoid sweeping the film off the glass. To evaluate qualitatively the nature of the observed inhibition, the reduction was repeated using a suspension of finely ground PPNVP, rather than films. The result is shown in FIG. 1d. The increased conversion thus reflects improved mixing and interfacial contact between polymer and reaction medium. The few remaining unreacted carbonyls may then be attributed to inaccessible groups, presumably constrained below the polymer surface. An implication of this result is that a thinner PPNVP film (<0.5 $\mu$m is more typical for a surface modification procedure) covalently bound to a polymer substrate could be reduced almost to completion. The hydroxyl groups could then be used in a subsequent modification procedures such as immobilization, which is of considerable importance for a wide range of biomedical applications.

In solution, reduction of carbonyl can be inhibited by steric factors or the presence of conjugated substituents (House, M. O. *Modern Synthetic Reactions*, second edition, Benjamin/Cummings, Menlo Park, Ch. 2, 1977). Additionally, in a biphasic system, the extent of reaction will be largely determined by the availability of reactive functional groups at the solid/liquid interface. The initial interfacial concentration of reactants is strongly influenced by the nature and extent of the polymer-solvent interactions. Thus, reduction of carbonyl in PPNVP by LiAlH$_4$ was not observed because THF is a non-solvent for the polymer. The work of Whitesides, et al. (Rasmussen, J. R., Stedronsky, E. R., Whitesides, G. M., *J. Am. Chem. Soc.*, 99, 4736, 1977; and, Rasmussen, J. R., Bergbreiter, D. E., Whitesides, G. M., *J. Am. Chem. Soc.*, 99, 4746, 1977) and Dias and McCarthy (Dias, A. J., McCarthy, T. J., *Macromolecules*, 17, 2529, 1984) infers that carbonyl groups located at the polymer surface (i.e. <10-Å depth a qualitative approximation based on the quantitative estimate of Dias and McCarthy, see ref. 19a, for a surface reaction in the presence of a "non-wetting" solvent) should have been reduced by LiAlH$_4$. However, for a 1.5-$\mu$m-thick PPNVP film and with assumption of a uniform spatial distribution of carbonyl groups, less than 0.1% of the total carbonyl were available for reaction. Such low conversion would not be detected by IR analysis of the bulk polymer. For significant reaction to occur, the carbonyl groups require sufficient mobility to approach the polymer surface and undergo solvation. In this way, an initial three-dimensional distribution of carbonyl is established in the liquid phase.

The phenomenon of functional group mobility in plasma-treated polymers has been the subject of several publications (Everhart, D. S., Reilley, C. N., *Surf. Interface Anal.*, 3, 126, 1981; and, Gerenser, L. J., Elman, J. F., Mason, M. G., Pochan, J. M., *Polymer*, 26, 1162, 1985) while the effects of the same phenomenon in crosslinked plasma-polymerized materials has not been studied in detail. However, as the inventors recently indicated, PPNVP shows considerable contact angle hysteresis with a water probe (Marchant, R. E., Yu, D., Khoo, C, J. *Polym. Sci., Polym. Chem.*, Vol. 27, pp. 881-895, 1989). This was attributed to reorientation effects that occur in the polymer surface in order to minimize the polymer-water interfacial free energy. As a good solvent for PPNVP, water is able to penetrate into the film, disrupt intermolecular associations such as hydrogen bonding, and swell the cross-linked polymer. Swelling of the PPNVP increases interchain spacing and segmental mobility, exposing additional carbonyl groups initially in the bulk polymer to the aqueous phase. Solvation of the carbonyl then enables the protonation and hydride ion transfer to occur.

Quantitative Estimation of Hydroxyl Groups

Figure 2:
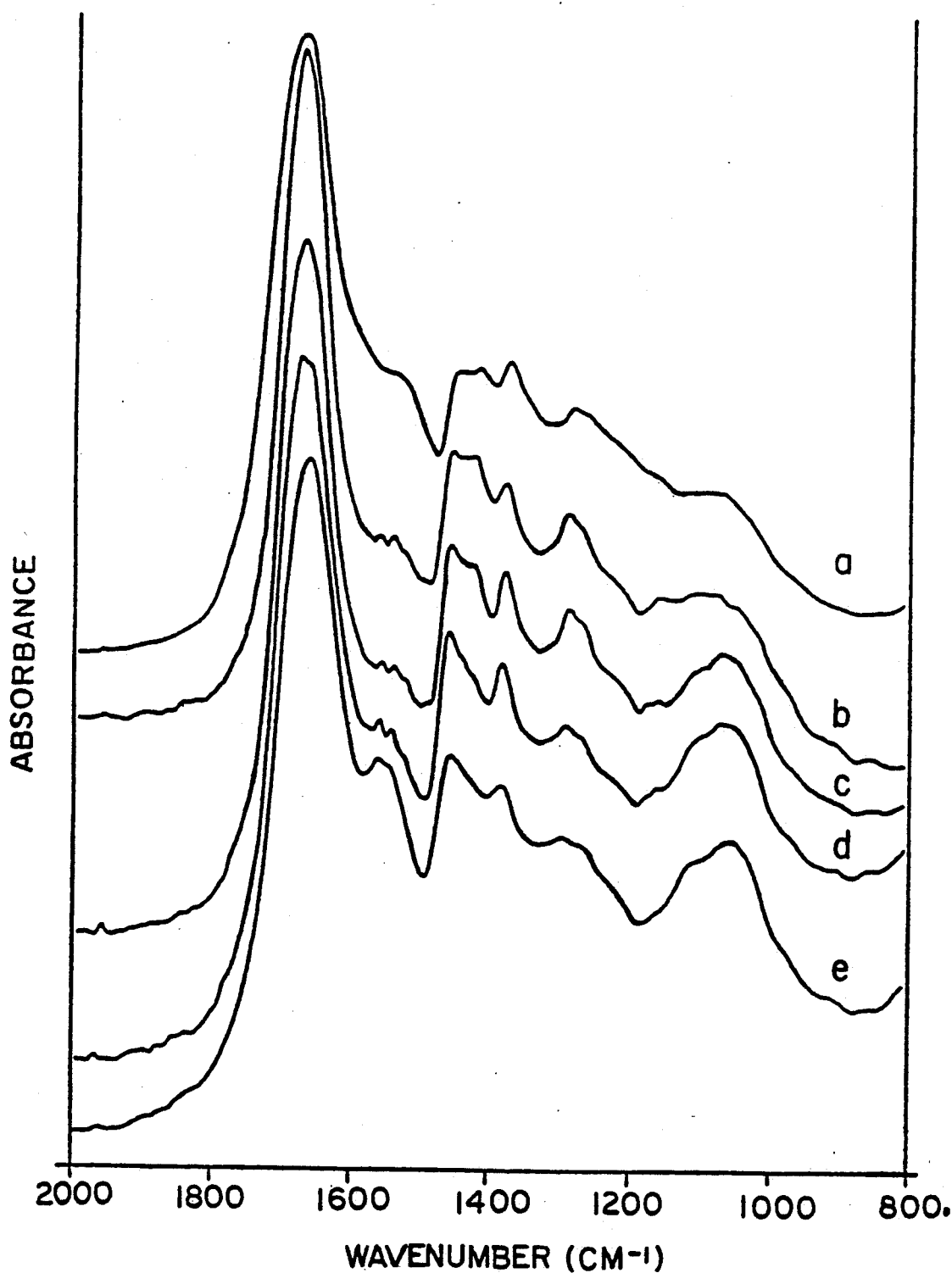
FIG. 2 is a graph demonstrating the FT-IR spectra, 2000–800 cm$^{-1}$ region, of PPNVP reduced in film form by 0.26 mol NaBH4 at room temperature for (a) 0 hours (original PPNVP); (b) 1 hour; (c) 5 hours; (d) 20 hours; and (e) 30 hours.

Determination of hydroxyl content in polymers using IR spectroscopy is usually accomplished by using the hydroxyl stretching absorption $\nu(O-H)$ at 3600-3200 cm$^{-1}$ (Boiko, V. P.; Grishchenko, V. K., *Acta Polymerica*, 36, 459, 1985). In the applicants' studies, the choice was complicated by the presence of nitrogen functional groups and the concomitant spectral interference from N—H absorptions in the 3500-3200 cm$^{-1}$ range. It became evident in the preliminary studies that the $\nu(C-O)$ of COH (Boiko, V. P., Grishchencko, J. F., Mason, M. G., Pochan, J. M., *Polymer.*, 26, 1162, 1985; and, Sato, Y., Hoshino, M., Ebisawa, F., *J. Appln. Polym. Sci.*, 26, 2053, 1981; and, Socrates, G., *In Infrared Characteristic Group Frequencies*, Wiley-Interscience, N.Y., Ch. 6, 1980; and, Chung, T. C., *Macromolecules*, 21, 865, 1988) at 1180-980 cm$^{-1}$ was very sensitive to the progress of the reaction. FIG. 2 and Table I below show the effect of reaction time on the intensity of the C—O stretching absorption. The relative intensity of this band increased with reaction time (up to about 20-30 hours). Hence, this absorption band was used in the determination of hydroxyl content.

TABLE I

Variation in Absorption Ratio ($\nu(C=O)/\nu(C-O)$) in PPNVP with Reaction Time

| Reaction Time (hrs) | Absorption Ratio Abs ($\nu(C=O)$)/Abs ($\nu(C-O)$) |
|---|---|
| 0 (i.e., PPNVP) | 14.50 |
| 0.5 | 9.53 |
| 1.0 | 8.98 |
| 4.0 | 4.19 |
| 5.0 | 4.33 |
| 8.0 | 3.84 |
| 12.0 | 3.32 |
| 20.0 | 3.04 |
| 30.0 | 2.65 |
| 48.0 | 3.11 |
| 30.0 (suspension) | 0.51 |

Reductions were carried out on PPNVP films in 0.25 mol aqueous NaBH$_4$.

Figure 3:
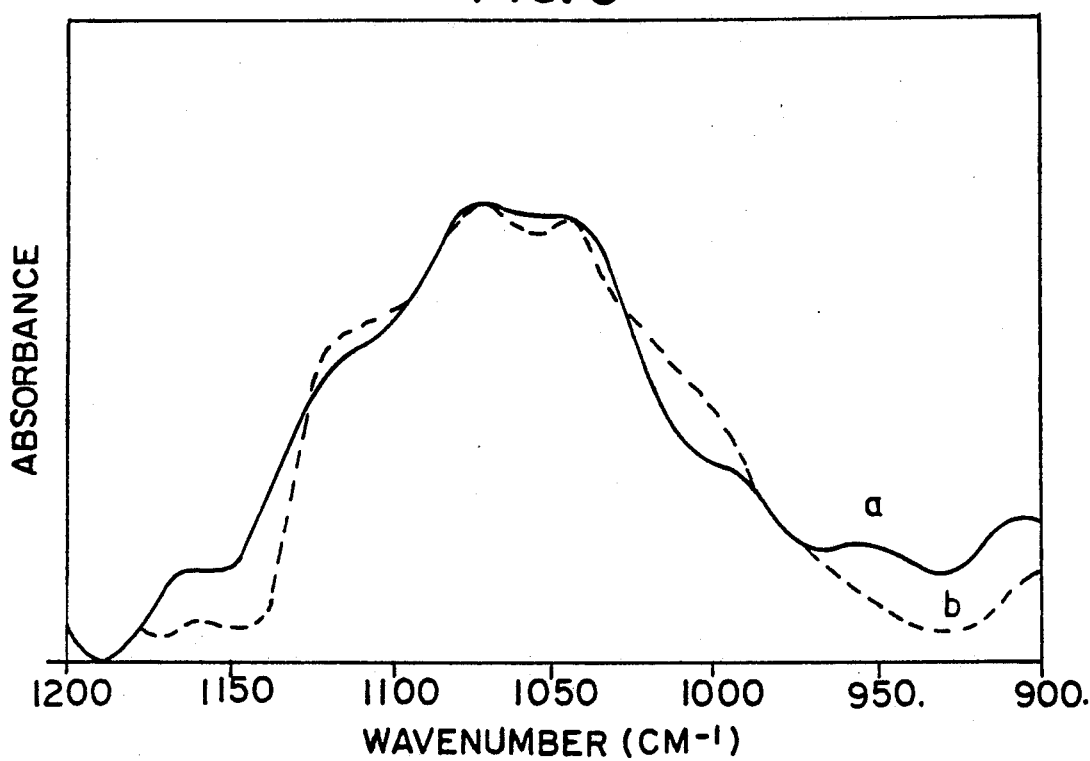
FIG. 3 is a graph showing the FT-IR spectra, 1200–900 cm$^{-1}$ region of (a) PPNVP reduced in film form by 0.26 mol NaBH4 for five hours (solid line); and (b) linear combination of PVA (scale factor = 1.00) and 1-hexadecanol (scale factor = 0.075) after shifting to lower wavenumbers by 25 cm$^{-1}$.

FIG. 3 provides the result of a typical curve-fitting procedure for the 1180-980 cm$^{-1}$ range, based on linear combinations of the reference spectra for PVA and 1-hexadecanol. The dashed spectrum in FIG. 3 is a linear combination of PVA and 1-hexadecanol in the ratio 1:0.075. The curve fitting analysis for all reduced PPNVP indicated that the hydroxyl contents consisted of greater than 90% secondary alcohol (see Table II below). Best fit was obtained by shifting the composite references spectrum to 25 cm$^{-1}$ lower wave numbers. Based on this analysis, the absorptions at 1075 and 1045 cm$^{-1}$ in reduced PPNVP were assigned to secondary and primary alcohol, respectively. This latter assignment is consistent with that recently observed for primary alcohol in a polyocten-8-ol. (Chung, T. C., *Macromolecules*, 21, 865, 1988). The $\nu(C-O)$ frequency in alcohols is sensitive to the molecular environment; hydrogen bonding, unsaturation, and chain branching all decrease the vibrational frequency (Socrates, G., *In Infrared Characteristic Group Frequencies*, Wiley-Interscience, N.Y., Ch. 6, 1980). Consequently, the required shift appears consistent with the different molecular environments between the reference compounds and the reduced PPNVP. In the absence of appropriate branched model compounds for the cross linked PPNVP, applicants used the two linear alcohols as reference compounds. The differences in hydrogen-bonding behavior and the effect of branching in PPNVP introduced a systematic error which diminished the accuracy of applicants' quantitative determinations. The results are therefore considered quantitative estimates only.

TABLE II

Formation of Hydroxyl Groups in PPNVP Films by Reduction With 0.26 mol Aqueous NaBH$_4$

| Reaction Time (h) | Percent 2° Hydroxyl of Total (%) | Increased Hydroxyl Content in Reduced PPNVP (mmol/g) | Maximum Hydroxyl in Reduced PPNVP (mmol/g) |
|---|---|---|---|
| 0 (i.e. PPNVP) | — | — | 1.87 |
| 0.5 | 96.9 | 0.58 | 2.45 |
| 1.0 | 94.5 | 0.71 | 2.58 |
| 4.0 | 93.4 | 1.62 | 3.49 |
| 5.0 | 95.4 | 1.71 | 3.58 |
| 12.0 | 93.4 | 1.99 | 3.86 |
| 20.0 | 92.3 | 1.92 | 3.79 |
| 30.0 | 91.2 | 2.27 | 4.14 |
| 48.0 | 92.3 | 2.22 | 4.09 |

Figure 4:
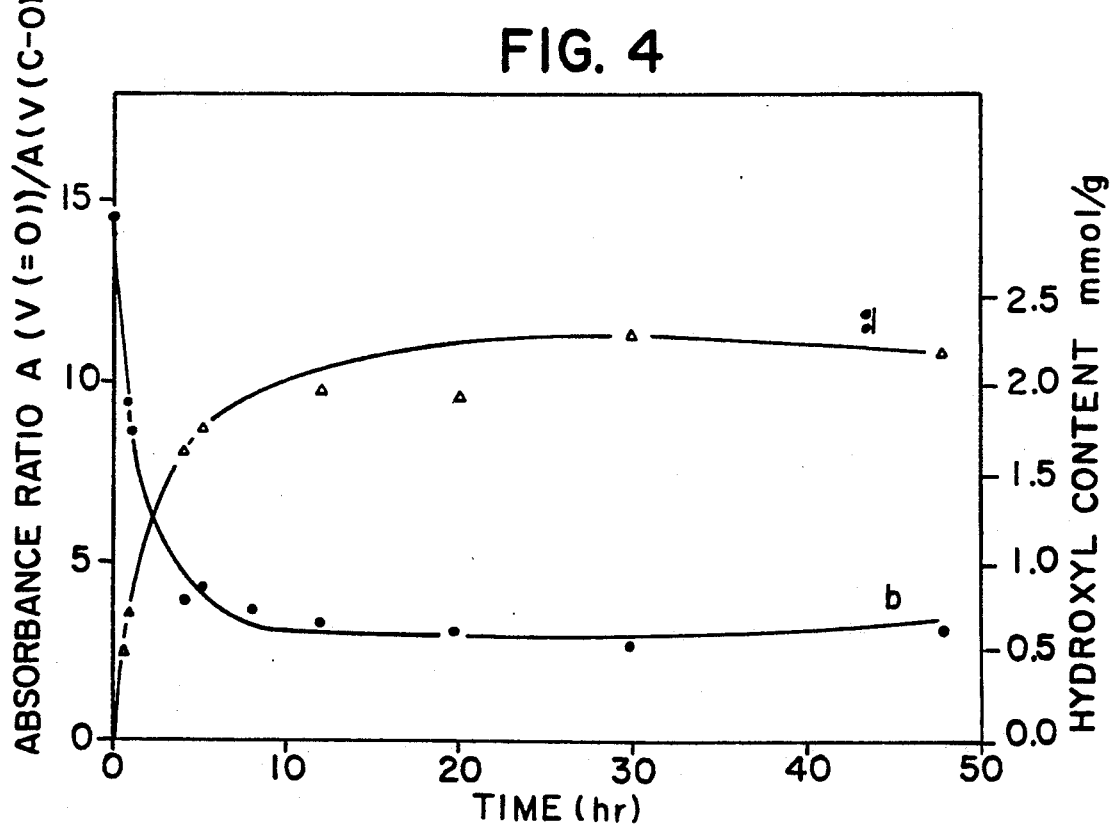
FIG. 4 is a graph demonstrating variation in IR (integrated) absorbance ratio: $A(\nu(C=O))/A(\nu(C-O))$, (·), and increased hydroxyl content (mmol/g), (Δ), in PPNVP films reduced by 0.26 mmol NaBH4, with reaction time.

The estimated increase in hydroxyl content in reduced PPNVP derived from the calibration curves for PVA and 1-hexadecanol are shown in FIG. 4 and Table II. The results reflect quantitatively the effectiveness of the reduction and its progress with reaction time. FIG. 4 includes the absorption rate of $\nu(C=O)$ at 1670 cm$^{-1}$ to $\nu(C-O)$ at 1180-980 cm$^{-1}$, which reflects the relative progress of the reaction time.

The applicants can attribute the increase in the $\nu(C-O)$ peak to increasing hydroxyl content in the polymers, since the same absorption in the PPNVP control is subtracted out in the calculations. This procedure minimizes errors caused by spectral overlap (e.g. from $\nu(C-C)$ vibrations). Consequently, the total hydroxyl content in the reduced polymers is probably somewhat higher than that reported in FIG. 4, since the hydroxyl content in the original PPNVP can be assumed to be greater than zero. To reflect this, the maximum total hydroxyl content has been included in Table II. These values assume that IR band at 1180-980 cm$^{-1}$ the original PPNVP consists entirely of $\nu(C-O)$ in COH and thus ignores other spectral contributions.

In summary, applicants have demonstrated that reproducible hydroxylated plasma-polymerized films can be obtained by using aqueous NaBH$_4$ as a reducing agent at room temperature. Water plays an important role in solvating the cross linked polymer and increasing the mobility of the carbonyl groups. Infrared analysis indicated that secondary alcohol was greater than 90% of the total hydroxyl content. Reduction increased the hydroxyl content in PPNVP films by up to 2.3 mmol/g. By reducing a suspension of PPNVP rather than films, the hydroxyl content was further increased.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A process for producing a hydroxylated plasma-polymerized N-vinyl-2-pyrrolidone polymer comprising the steps of:
   a) plasma-polymerizing N-vinyl-2-pyrrolidone monomers to produce an insoluble plasma-polymerized N-vinyl-2-pyrrolidone polymer; and
   b) reducing the carbonyl groups in the insoluble plasma-produced N-vinyl-2-pyrrolidone polymer to alcohol groups by chemical reduction using an aqueous solution of sodium borohydride.

2. The hydroxylated plasma-polymerized N-vinyl-2-pyrrolidone polymer produced by the process of claim 1.

3. The process of claim 1, wherein said plasma-polymerization step is radio frequency plasma-polymerization.

4. The process of claim 1, wherein said plasma-polymerized N-vinyl-2-pyrrolidone is a powdered form.

5. A process for producing a hydroxylated plasma-polymerized N-vinyl-2-pyrrolidone film comprising the steps of:
   a) plasma-polymerizing N-vinyl-2-pyrrolidone monomers to produce an insoluble plasma-polymerized N-vinyl-2-pyrrolidone film; and
   b) immersing the insoluble plasma-polymerized N-vinyl-2-pyrrolidone film in an aqueous solution of sodium borohydride thereby reducing the carbonyl groups in the plasma-polymerized film to hydroxyl groups.

6. The hydroxylated plasma-polymerized N-vinyl-2-pyrrolidone film produced by the process of claim 5.

7. The process of claim 5, wherein aid plasma-polymerization step is by radio frequency plasma polymerization.

8. A process for producing a hydroxylated plasma-polymerized polymer comprising the steps of:
   a) utilizing a plasma polymerization process to synthesize an insoluble plasma-polymerized polymer; and
   b) adding the synthesized insoluble plasma-polymerized polymer an aqueous solution of a metal hydride thereby reducing the carbonyl groups in the plasma-polymerized polymers to hydroxyl groups.

9. The hydroxylated plasma-polymerized polymer produced by the process of claim 8.

10. The process of claim 8, wherein said metal hydride is sodium borohydride.

11. A process for producing a hydroxylated plasma-polymerized N-vinyl-2pyrrolidone polymer comprising the steps of:
    a) plasma-polymerizing N-vinyl-2-pyrrolidone monomers to produce an insoluble plasma-polymerized N-vinyl-2-pyrrolidone polymer rich in carbonyl groups; and
    b) reducing the carbonyl groups in the insoluble plasma-produced N-vinyl-2-pyrrolidone polymer to alcohol groups by chemical reduction using an aqueous solution of sodium borohydride.

12. The hydroxylated plasma-polymerized N-vinyl-2-pyrrolidone polymer produced by the process of claim 11.

13. The process of claim 11, wherein said plasma-polymerization step is radio frequency plasma-polymerization.

14. The process of claim 11, wherein said plasma-polymerized N-vinyl-2-pyrrolidone is in powdered form.

* * * * *